United States Patent
Xu et al.

(10) Patent No.: US 10,828,508 B2
(45) Date of Patent: Nov. 10, 2020

(54) DETECTING COLLISION

(71) Applicant: Shanghai Neusoft Medical Technology Co., Ltd., Shanghai (CN)

(72) Inventors: Long Xu, Shenyang (CN); Dong Wang, Shenyang (CN); Wenda Qin, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 0 days.

(21) Appl. No.: 16/293,174

(22) Filed: Mar. 5, 2019

(65) Prior Publication Data

US 2019/0275351 A1    Sep. 12, 2019

(30) Foreign Application Priority Data

Mar. 6, 2018    (CN) .......................... 2018 1 0183503

(51) Int. Cl.
*A61N 5/10*    (2006.01)

(52) U.S. Cl.
CPC ......... *A61N 5/1037* (2013.01); *A61N 5/1039* (2013.01); *A61N 5/1048* (2013.01); *A61N 5/103* (2013.01); *A61N 5/1042* (2013.01); *A61N 2005/1092* (2013.01)

(58) Field of Classification Search
CPC .... A61N 5/1048; A61N 5/103; A61N 5/1042; A61N 5/1039; A61N 5/1037
See application file for complete search history.

(56) References Cited

U.S. PATENT DOCUMENTS

2016/0166856 A1 * 6/2016 Popple ..................... A61B 6/08
600/1

FOREIGN PATENT DOCUMENTS

| CN | 101022851 A   | 8/2007 |
| CN | 101947360 A   | 1/2011 |
| CN | 202263308 U   | 6/2012 |
| WO | 2017136551 A1 | 8/2017 |

OTHER PUBLICATIONS

State Intellectual Property Office of the People's Republic of China, Office Action and Search Report Issued in Application No. 201810183503.5, dated Oct. 9, 2019, 14 pages,(Submitted with English-language Machine Translation).

* cited by examiner

*Primary Examiner* — David P Porta
*Assistant Examiner* — Fani Boosalis
(74) *Attorney, Agent, or Firm* — Fish & Richardson P.C.

(57) ABSTRACT

Methods, apparatus and systems for detecting collision are provided. In one aspect, a method includes: obtaining a first model by performing modelling based on an exterior shape of a first component in the target system, the first component being a movable component, obtaining a second model by performing modelling based on an exterior shape of a second component in the target system, the second component being different from the first component, determining a spatial position of the first model and a spatial position of the second model according to a movement process of the first component at each of detection timings, and for each of the detection timings, determining whether the first component collides with the second component according to the spatial position of the first model, the spatial position of the second model, and a collision condition.

21 Claims, 7 Drawing Sheets

DETECTING COLLISION

CROSS REFERENCE TO RELATED APPLICATIONS

This application claims priority to Chinese Patent Application No. 201810183503.5 filed on Mar. 6, 2018, the entire content of which is incorporated herein by reference.

BACKGROUND

Medical linear accelerator systems are mainly used to perform radiotherapy treatment for malignant tumors. In a treatment process, many components of a medical linear accelerator system, such as a treatment bed, a treatment head and a gantry, may move.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, and systems for detecting collision in a target system including at least one movable component, e.g., a medical linear accelerator system, which can determine whether a collision between components will occur by simulating spatial positions of the components without using a collision-sensing apparatus.

In general, one innovative aspect of the subject matter described in this specification can be embodied in methods that include the actions of detecting collision for a target system including at least one movable component, including: obtaining a first model by performing modelling based on an exterior shape of a first component in the target system, the first component being a movable component; obtaining a second model by performing modelling based on an exterior shape of a second component in the target system, the second component being different from the first component; determining a spatial position of the first model and a spatial position of the second model according to a movement process of the first component at each of detection timings; and for each of the detection timings, determining whether the first component collides with the second component according to the spatial position of the first model, the spatial position of the second model, and a collision condition.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. For example, determining whether the first component collides with the second component can include: determining whether the spatial position of the first model and the spatial position of the second model satisfy the collision condition, and the collision condition can refer to that the first model and the second model contact with each other.

In some implementations, the movement process of the first component is pre-simulated before a real movement process of the first component.

In some implementations, the movement process of the first component is simulated approximately synchronously with a real movement process of the first component. In some examples, the actions further include: for each of the detection timings in the movement process, determining the spatial position of the first model and the spatial position of the second model at a detection period subsequent to the detection timing; determining whether the first model and the second model contact with each other at the detection period in a simulation based on the spatial position of the first model and the spatial position of the second model at the detection period; and determining whether the first component will collide with the second component at the detection period in the real movement process based on a result of determining whether the first model and the second model contact with each other at the detection period in the simulation. The actions can further include: in response to determining that the first component will collide with the second component at the detection period in the real movement process, terminating a corresponding operation plan of the target system by at least one of stopping each moving component in the target system or prompting safety warning information to a user.

In some implementations, the actions further include: setting a first rigidbody assembly and a first collider assembly for the first model; and setting a second rigidbody assembly and a second collider assembly for the second model.

In some implementations, determining whether the first component collides with the second component includes: setting a first boundary for the first model, where, there is a first boundary gap between the first boundary and a boundary of the first model, and a value of the first boundary gap is equal to or greater than zero; setting a second boundary for the second model, where, there is a second boundary gap between the second boundary and a boundary of the second model, and a value of the second boundary gap is equal to or greater than zero; for each of the detection timings, determining whether a boundary overlapping occurs between the first boundary and the second boundary according to the spatial position of the first model and the spatial position of the second model; and in response to determining that the boundary overlapping occurs between the first boundary and the second boundary, determining that the first component collides with the second component.

In some cases, when the value of the first boundary gap is equal to zero, a range enclosed by the first boundary is consistent with the exterior shape of the first model; when the value of the first boundary gap is greater than zero, a range enclosed by the first boundary includes the first model; when the value of the second boundary gap is equal to zero, a range enclosed by the second boundary is consistent with the exterior shape of the second model; and when the value of the second boundary gap is greater than zero, a range enclosed by the second boundary includes the second model.

In some examples, determining whether a boundary overlapping occurs between the first boundary and the second boundary includes: determining a spatial position of the first boundary based on the spatial position of the first model and the value of the first boundary gap; determining a spatial position of the second boundary based on the spatial position of the second model and the value of the second boundary gap; and determining whether the boundary overlapping occurs between the first boundary and the second boundary based on the spatial position of the first boundary and the spatial position of the second boundary.

The boundary overlapping can include any one of: a point contact, a line contact, a surface contact, and a block contact.

The target system can include a medical linear accelerator system, the first component can include a treatment head of the medical linear accelerator system, and the second component can include a treatment bed of the medical linear accelerator system. Determining the spatial position of the first model and the spatial position of the second model can include: obtaining a radiotherapy treatment plan of a subject to be treated; and determining the spatial position of the first model and the spatial position of the second model according to the movement process of the first component recorded in the radiotherapy treatment plan at each of the detection timings.

In some cases, the actions further include: during a process of performing treatment for the subject according to the radiotherapy treatment plan, obtaining a third model by performing modelling based on an exterior shape of the subject. The actions can further include: determining a spatial position of the third model at each of the detection timings; and for each of the detection timings, determining whether the first component collides with the subject according to the spatial position of the first model, the spatial position of the third model and the collision condition.

In some cases, obtaining the third model by performing modelling based on the exterior shape of the subject includes: obtaining three-dimension (3D) image data of the subject with a 3D camera; and obtaining the third model by performing the modelling based on the three-dimension image data of the subject. The actions can further include: at each of the detection timings, determining a spatial position of the third model based on the movement process of the first component; and adjusting the spatial position of the third model based on dynamic 3D image data of the subject real-time transmitted from the 3D camera.

In some cases, determining whether the first component collides with the subject includes: setting a first boundary for the first model, where, there is a first boundary gap between the first boundary and a boundary of the first model, and a value of the first boundary gap is equal to or greater than zero; setting a third boundary for the subject, where, there is a third boundary gap between the third boundary and a boundary of the third model, and a value of the third boundary gap is equal to or greater than zero; for each of the detection timings, determining whether a boundary overlapping occurs between the first boundary and the third boundary according to the spatial position of the first model and the spatial position of the third model; and in response to determining that the boundary overlapping occurs between the first boundary and the third boundary, determining that the first component collides with the subject. The boundary overlapping can include any one of: a point contact, a line contact, a surface contact, and a block contact.

In some cases, the movement process of the first component is simulated approximately synchronously with a real movement process of the first component, and the actions can further include: for each of the detection timings in the movement process, determining the spatial position of the first model at a detection period subsequent to the detection timing and the spatial position of the third model at the detection timing; determining whether the first model and the third model contact with each other at the detection period in a simulation based on the spatial position of the first model at the detection period and the spatial position of the third model at the detection timing; and determining whether the first component will collide with the third component at the detection period in the real movement process based on a result of determining whether the first model and the third model contact with each other at the detection period in the simulation.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

BRIEF DESCRIPTION OF DRAWINGS

Like reference symbols in the various drawings indicate like elements.

DETAILED DESCRIPTION

Figure 1:
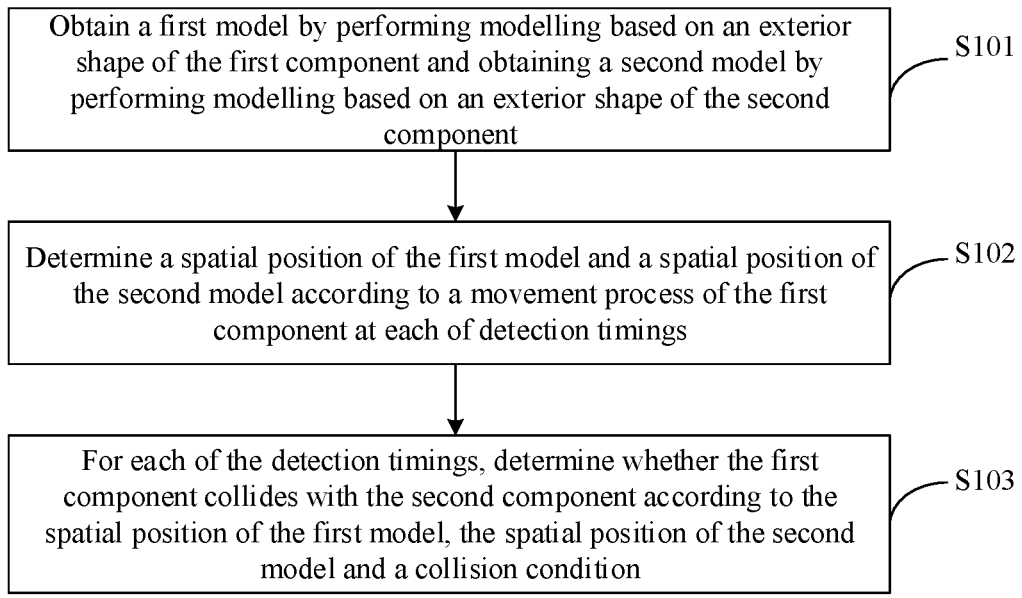
FIG. 1 is a flowchart illustrating a process of a method of detecting collision according to an example of the present disclosure.

In a medical linear accelerator system, the system may have a plurality of moving components, such as a treatment head, a treatment bed, and a gantry. These components may collide with each other during a movement process, and thus the medical linear accelerator system may be damaged and the safety of a user (for example, a doctor or an operator) and a subject (for example, a patient) may also be harmed.

In an example, a collision-sensing apparatus is mounted for a treatment head. During an operation process of the treatment head, whether another component enters a preset protection zone at a lower surface of the treatment head may be detected by the collision-sensing apparatus. If the collision-sensing apparatus detects that the treatment bed enters the preset protection zone, it indicates that the treatment head is likely to collide with the treatment bed. At this time, the treatment head can be stopped and/or a safety warning can be prompted to prevent a physical collision between the treatment head and the treatment bed. However, because the medical linear accelerator system has many components which are different in shape and the medical linear accelerator system has a plurality of complex moving trajectories, it is impossible to mount collision-sensing apparatuses everywhere. Thus, the collision-sensing apparatuses are mounted only at specific positions of some components to prevent collisions between these components. Further, the collision-sensing apparatus occupies a space, bringing inconvenience to a normal operation process.

In view of this, an implementation of the present disclosure provides a method of detecting collision. In this method, all components in a target system or individual components that may collide with each other in the target system, may be separately modelled, and a real movement process of each component is simulated by using the model of each component. During simulation, whether respective component models collide with each other may be determined, so that whether respective components collide with each other in a real movement process can be determined based on the simulation result.

It is noted that the method of detecting collision in the present disclosure is applied to a target system including at least one movable component. The target system is not limited in type in the present disclosure. The target system may be a medical linear accelerator system and may also be another system with a movable component. In a practical application, when the target system is in an operating state, some components included in the target system may move. For example, the treatment bed, the treatment head and the gantry and so on in the medical linear accelerator system may move during a radiotherapy treatment process. Those components that will move in the target system are defined as movable components. Those components that will not move in the target system are defined as immovable components.

The method of detecting collision provided in the present disclosure can be described in detail below in combination with specific examples.

FIRST EXAMPLE

In the example, a movable component of a target system to be detected is taken as a first component, and a movable component or an immovable component of the target system other than the first component is taken as a second component.

FIG. 1 is a flowchart illustrating a process of a method of detecting collision according to the example. The process of the method of detecting collision may include the following steps.

At step S101, a first model is obtained by performing modelling based on an exterior shape of the first component, and a second model is obtained by performing modelling based on an exterior shape of the second component.

In the example, the actual size parameters of the first component and the second component may be obtained by measuring each component, or obtained from a database of a component manufacturer, a local database of the target system, or other data-obtaining channels. Then, a three-dimension (3D) model can be obtained by performing 3D modelling based on the actual size parameters, which reflect the exterior shape, of the first component. This 3D model may be defined as the first model. Also, another 3D model can be obtained by performing 3D modelling based on the actual size parameters, which reflect the exterior shape, of the second component. This 3D model may be defined as the second model.

It is noted that the first model and the second model may be models obtained by performing proportionally scaling for the first component and the second component.

For example, the target system is a linear accelerator system, the first component is a treatment head, and the second component is a medical treatment bed. Since components of a linear accelerator system manufactured by different manufacturers may be different in exterior shape, the actual size parameters of the treatment head and the treatment bed may be firstly obtained from databases of the dedicated component manufacturers. Then 3D modelling is performed for the treatment head and the treatment bed based on the actual size parameters, respectively. The actual size parameters of each component shall be the correct data of the corresponding component. If there is an error with the data, collision detection results based on the models may be impacted.

At step S102, a spatial position of the first model and a spatial position of the second model are determined based on a movement process of the first component at each of detection timings.

To prevent respective components in the target system from colliding with each other in a real movement process, as an example, an operating trajectory of each component may be pre-simulated to perform collision prediction. An operation plan of each component in the target system may be pre-obtained, an operating trajectory set for the first component may be determined from the operation plan, that is, the moving process of the first component is known. Taking a medical linear accelerator system as an example, the operation plan may be as follows: after the treatment bed moves under the treatment head, the treatment head moves to a position 10 centimetres above the abdomen of a subject to be treated and starts performing irradiation onto the subject until the irradiation is ended, and finally the treatment head moves to its original place. Thus, the movement process of the treatment head may be determined based on the operation plan. Therefore, before the first component and the second component are controlled to perform real movements based on the operation plans, the movement process of the first component may be simulated by using the first model. In case that the second component also moves, the movement process of the second component may be simulated by using the second model. In case that the second component does not move, the spatial position of the second component may be determined by using the second model. According to the movement process, a plurality of detection timings may be set to determine the spatial position of the first model and the spatial position of the second model at each of the detection timings. Still taking the medical linear accelerator system as an example, the simulated movement process may include the spatial positions of the treatment head and the treatment bed in a period from the time that the treatment head starts moving to the time that the treatment head moves back to its original place. The set detection timings may be a detection timing every 0.1 second (s) in the period. The time interval is only illustrative, and may be set according to actual needs.

To determine whether respective components in the target system collide with each other in a real movement process, as an example, a movement process of each component may be simulated approximately synchronously so that a real-time collision detection is performed. Specifically, an operation plan of each component in the target system may be pre-obtained and a movement process set for the first component is determined from the operation plan. In this way, when the first component and the second component are controlled to perform real movement based on the operation plan, the spatial positions of the first component are simulated by using the first model and the spatial positions of the second component are simulated by using the second model. That is, at each detection timing of the movement process, the spatial positions of the first model and the spatial positions of the second model at a subsequent detection period may be pre-determined. The duration of the detection period may include at least from the particular detection timing to a detection timing next to the particular detection timing. Still taking the above medical linear accelerator system as an example, when the movement process proceeds to the detection timing of 0.1 s, it is desired to determine the spatial positions of each model in a period after 0.1 s, e.g., the spatial positions of each model from 0.1 s to 0.2 s. When the movement process proceeds to the detection timing of 0.2 s, it is desired to determine the spatial positions of each model in a period after 0.2 s, e.g., the spatial position of each model from 0.2 s to 0.3 s. The above duration of detection period is only illustrative, and may be set according to actual needs.

At step S103, for each of the detection timings, whether the first component and the second component collide with each other is determined according to the spatial position of the first model, the spatial position of the second model, and a collision condition, for example, by determining whether the spatial positions of the first model and the second model satisfy the collision condition. The collision condition can be that the first model and the second model contact with each other.

If the movement process of each component is pre-simulated at step S102, that is, before a real movement process, whether the first model and the second model will contact with each other in a simulation environment is determined based on the spatial positions of the first model and the spatial positions of the second model at the detection timings in the movement process, and the collision condition. If it is determined that the first model and the second model will contact with each other in the simulation environment, e.g., in one or more particular detection timings, it is predicted that the first component will collide with the second component in a real movement process. Otherwise, it is predicted that no collision will occur in the real movement process.

Further, if the pre-simulated result indicates that the first component and the second component will collide with each other in the real movement process, the target system may be forbidden to perform the corresponding operation plan. For example, prompt information representing "components collision may occur" may be output by voice, lamp light, text, or a combination thereof to prompt a user that the operation plan cannot be implemented, so that the user can cancel the operation plan.

If the movement process of each component is simulated approximately synchronously at step S102, e.g., during a real movement process, for each of the detection timings in the movement process, whether the first model and the second model contact with each other at the detection period in a simulation environment may be determined based on the spatial positions of the first model and the second model at a detection period subsequent to the detection timing. If it is determined that the first model and the second model contact with each other at the detection period in the simulation environment, it is determined that the first component will collide with the second component in the detection period in the real movement process, otherwise it is determined no collision will occur. Since all detection timings can cover the entire movement process of the first component, the detection periods after each of the detection timings can cover the entire movement process, too. Therefore, it is possible to detect in real-time whether the components are about to collide with each other during the entire movement.

Further, if a real-time detection result indicates that the first component and the second component will collide with each other in the detection period, a corresponding operation plan of the target system will be terminated. That is, each moving component is stopped, and also prompt information representing "components collision may occur" may be output by voice, lamp light, text, or a combination thereof to prompt a user to perform further processing.

To sum up, in a method of detecting collision provided by the example of the present disclosure, a movable component to be detected is taken as the first component, a movable component or an immovable component other than the first component is taken as a second component. A first model is obtained by performing modelling based on exterior shape of the first component, and a second model is obtained by performing modelling based on exterior shape of the second component. Then, the spatial position of the first model and the spatial position of the second model may be determined at each detection timing based on a movement process of the first component. Whether the first component and the second component collide with each other is determined at each detection timing based on the spatial position of the first model and the spatial position of the second model at the detection timing, and a collision condition. It can be seen that whether a collision will occur between components may be determined by simulating the spatial positions of the components without using a collision-sensing apparatus.

SECOND EXAMPLE

In the example, the target system may be a radiotherapy treatment system, for example, a medical linear accelerator system. Based on this, step S102 in the first example will be described in further detail herein.

Figure 2:
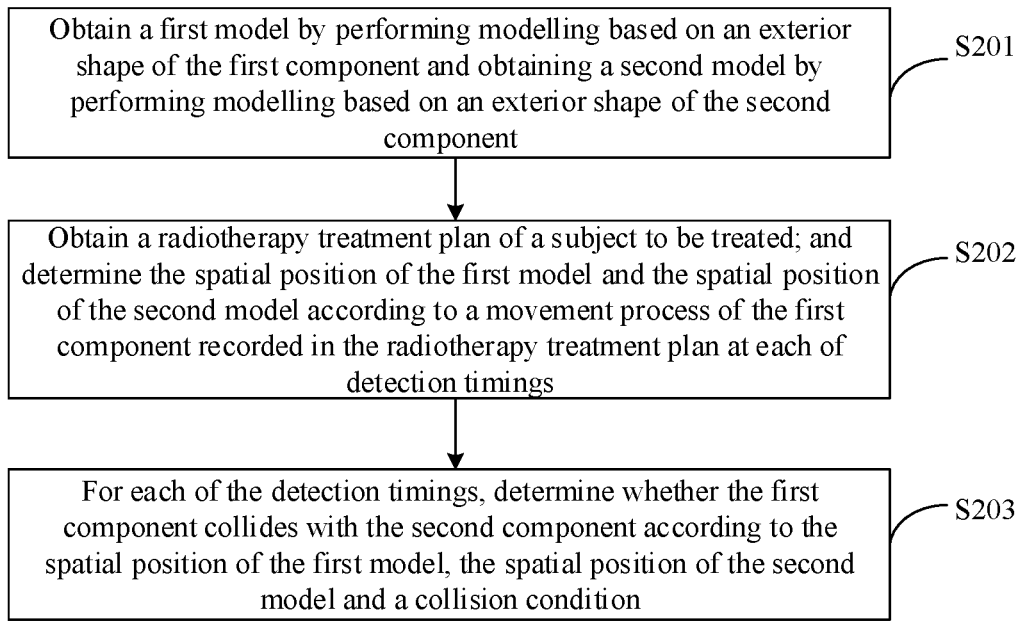
FIG. 2 is a flowchart illustrating a process of a method of detecting collision according to another example of the present disclosure.

FIG. 2 is a flowchart illustrating a process of a method of detecting collision according to the example. The method of detecting collision may include the following steps.

At step S201, a first model is obtained by performing modelling based on an exterior shape of the first component and a second model is obtained by performing modelling based on an exterior shape of the second component.

It is noted that step S201 is consistent with step S101 in the first example and a reference may be made to the descriptions of the first example for related parts which will not be repeated herein.

More specifically, component modelling may be performed in the following manner at step S201 in the example and step S101 in the first example.

Figure 3:
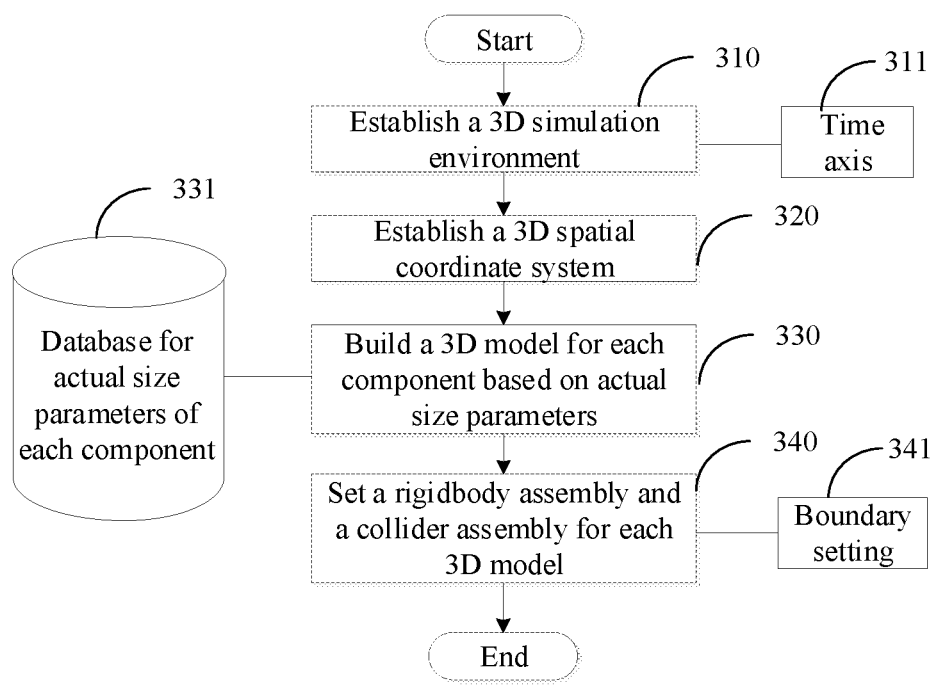
FIG. 3 is a flowchart illustrating a modelling process according to an example of the present disclosure.

As shown in FIG. 3, a 3D simulation environment may be established (310) by using a Unity 3D model development tool and a 3D spatial coordinate system may be established (320) in the 3D simulation environment. Then, a 3D model of the first component, i.e., the first model, and a 3D model of the second component, i.e., the second model, are built (330) in the 3D spatial coordinate system based on component size parameters obtained from a database (331), that is, actual size parameters of the first component and the second component. In addition, a time axis (311) may also be established in the simulation environment so that each model in the simulation environment corresponds to the time axis. In this way, spatial positions of each model may be controlled in a same time sequence during a collision detection. It can be seen that each model in the simulation environment may be allowed to perform simulations both in space and time for the components (and a subject to be treated mentioned subsequently) of the target system by establishing the 3D spatial coordinate system and the time axis in the simulation environment.

To detect whether a collision occurs between components in the simulation environment, it is also required to set a rigidbody assembly and a collider assembly for the first model and set a rigidbody assembly and a collider assembly for the second model (340).

A rigidbody assembly may allow a model to be moved under controls of a physical system in the simulation environment. The model added with a rigidbody assembly may receive an external force and a torque force from the simulation environment to ensure that the model can move as it is in a real world. That is, only a model added with a rigidbody assembly can be affected by an external force, so as to simulate performances of a corresponding real component when subjected to the external force. In addition, collision can be triggered only when a collider assembly and a rigidbody assembly are both added to a model. That is, for two models added with rigidbody assemblies only, if the two models collide with each other, the models may pass through each other without collision in the simulation environment. A physics engine of the simulation environment can calculate the collision of the two models only when the two models are both added with the collider assemblies. Further, a boundary gap may be set (341) for the model. The specific description of the boundary settings can be found in the following example.

At step S202, a radiotherapy treatment plan of a subject to be treated is obtained; and a spatial position of the first model and a spatial position of the second model are determined based on a movement process of the first component recorded in the radiotherapy treatment plan at each of detection timings.

The subject to be treated can be a patient. Before performing radiotherapy treatment for the patient by using the radiotherapy treatment system, a doctor may prepare a set of radiotherapy treatment plans in advance. In the radiotherapy treatment plans, an operation plan of each component in the radiotherapy treatment system may be involved. Thus, the movement process of the first component may be determined from the operation plans. At the same time, it is determined whether the second component is in a stationary state or in a moving state and what is a movement process in the moving state.

For example, the first component is a treatment head, and the second component is a treatment bed. Based on the radiotherapy treatment plan prepared by the doctor, it may be determined when the treatment head and/or the treatment bed are in stationary states and when the treatment head and/or the treatment bed are in a moving state in addition to a moving direction, a moving amplitude, a moving speed, and so on. Thus, the movement processes of the treatment head and the treatment bed may be determined based on the information, thereby simulating their spatial positions in the simulation environment.

It is noted that step S202 is similar to step S102 in the first example and a reference may be made to descriptions of the first example for the related parts which are not repeated herein. As mentioned at step S102 in the first example, the movement process of each component may be pre-simulated and may also be simulated approximately synchronously, which is further described below.

Figure 4:
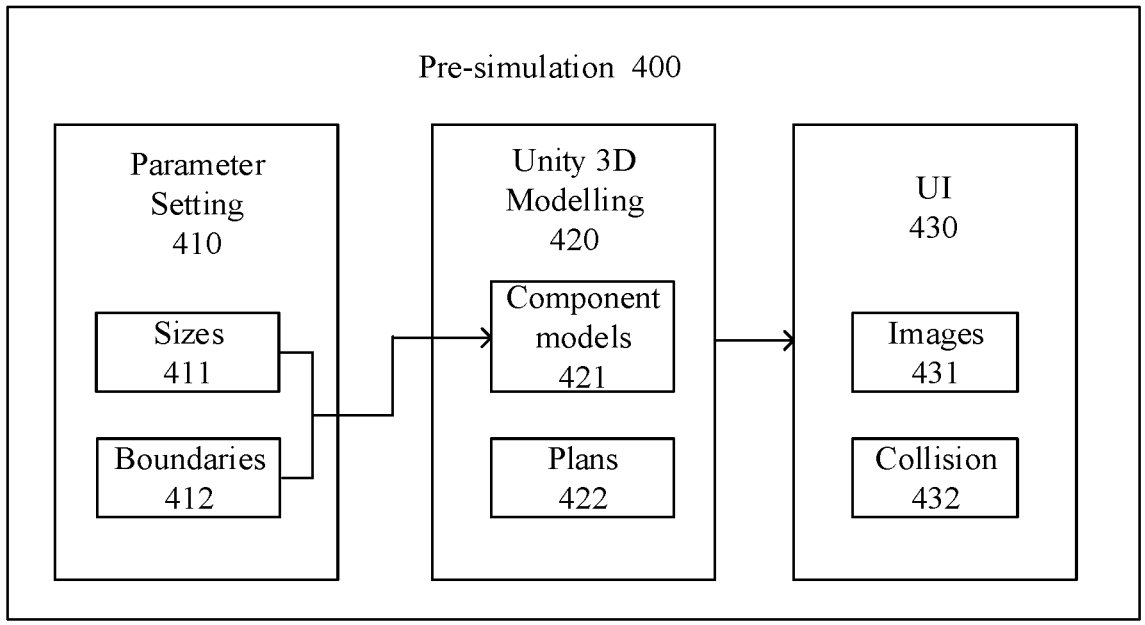
FIG. 4 is a block diagram illustrating a pre-simulation process according to an example of the present disclosure.

FIG. 4 illustrates a block diagram of a pre-simulation process 400. If it is desired to pre-simulate the movement process of each component, 3D modelling may be performed for respective components of the radiotherapy treatment system in the 3D simulation environment. For example, respective component models 421 may be determined by using a Unity 3D model development tool 420 as shown in FIG. 4. Actual size parameters 411 of a component provided by a parameter setting module 410 are used in building a corresponding model. Before radiotherapy treatment is performed for a patient based on a radiotherapy treatment plan 422, for each detection timing of the simulated movement process, component states are simulated with a 3D model so that spatial positions of the respective components are determined.

Figure 5:
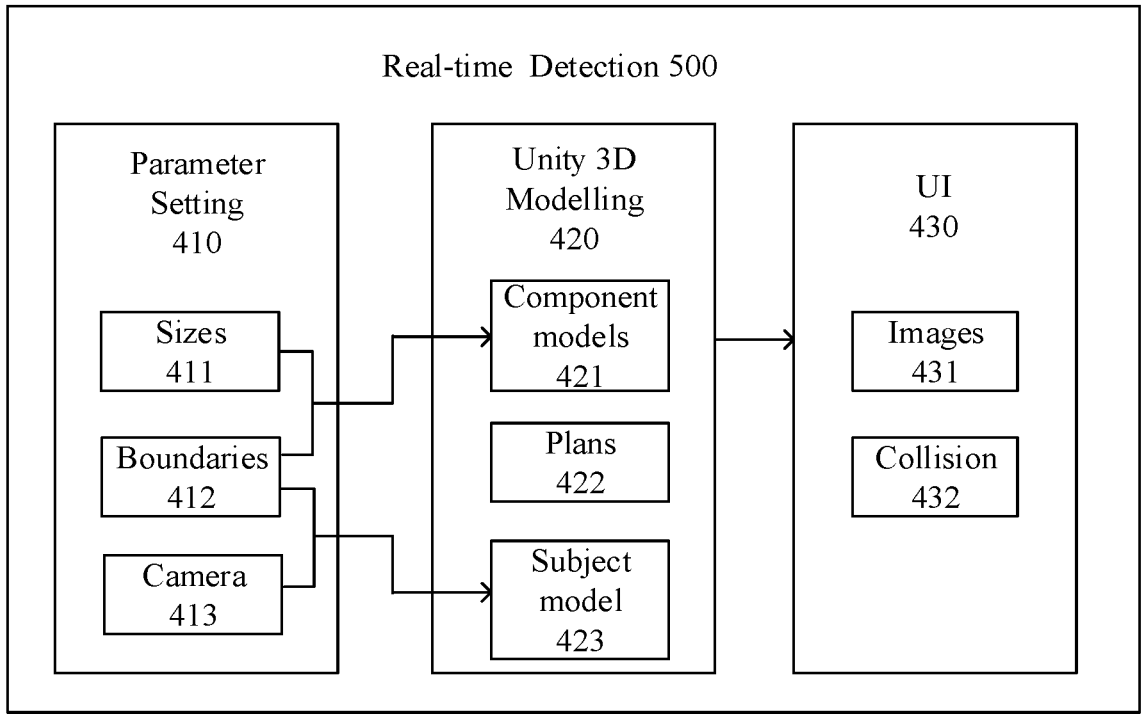
FIG. 5 is a block diagram illustrating a real-time detection process according to an example of the present disclosure.

FIG. 5 illustrates a block diagram of a real-time detection process 500. If it is desired to simulate the movement process of each component approximately synchronously, 3D modelling may also be performed for respective components of the radiotherapy treatment system in the 3D simulation environment. For example, respective component models 421 may be determined by using a Unity 3D model development tool 420 as shown in FIG. 5. Actual size parameters 411 of a component provided by a parameter setting module 410 are used in building a corresponding model. Further, since some components may also collide with a patient when performing radiotherapy treatment for the patient based on the radiotherapy treatment plan 422, 3D modelling for the patient can be also performed during the radiotherapy treatment process. For each detection timing of the movement process recorded in the radiotherapy treatment plan, states of the components and the patient can be simulated with the 3D models so that spatial positions of the respective components and the patient at a detection period subsequent to each detection timing may be determined.

Thus, in one implementation of the example, the following may be further included: during a process of performing treatment for the subject based on the radiotherapy treatment plan, a third model is obtained by performing modelling based on an exterior shape of the subject. When modelling is performed for the subject based the exterior shape, 3D image data of the subject may be obtained by a 3D camera. The third model is obtained by performing modelling based on the 3D image data. As shown in FIG. 5, 3D image data of the subject may be obtained with a camera 413 and thus, a model of the subject 423 can be determined by using the Unity 3D model development tool 420. The model of the subject 423 may be taken as the third model.

For example, a treatment head is taken as the first component, a treatment bed is taken as the second component, and the subject is a patient. Before radiotherapy treatment is performed for the patient, the patient needs to be placed on the treatment bed. A 3D camera, e.g., an orthographic camera or a perspective camera, may be pre-mounted above the treatment bed or at other directions. In this way, when treatment is performed for the patient based on a radiotherapy treatment plan, 3D image data of the patient may be obtained in real-time by using the 3D camera and real-time modelling is performed for the patient based on the 3D image data to obtain the third model. Further, the patient can be scaled proportionally to the treatment head and the treatment bed to get the third model that is proportional to the first model and the second model. As shown in FIG. 5, during a treatment process, the 3D camera 413 can obtain the body shape of the patient in real-time. Each obtaining timing (for example, every 0.5 s) may be pre-configured or set to a system default value. The dynamic 3D image data of the patient is transmitted to Unity 3D system 420 in real-time to correct the body position of the patient, where the body position may affect the body shape. In this way, the spatial positions of the patient can be accurately simulated.

Based on the above modelling result, the following may be further included in the example: the spatial position of the third model at each detection timing is determined. It is noted that although the movement process of the patient is unknown after the patient is placed in the treatment bed, the patient can be immobilized on the treatment bed and controlled by a user (for example, a doctor). Thus, the spatial position of the third model at the current detection timing can be taken as the spatial position of the third model at a detection period subsequent to the current detection timing to perform collision detection in cooperation with the spatial positions of the first model at the same detection period.

At step S203, for each of the detection timings, whether the first component and the second component collide with each other is determined based on the spatial position of the first model, the spatial position of the second model, and a collision condition.

It is noted that step S203 is consistent with step S103 in the first example and a reference may be made to the descriptions of the first example for related parts which are not repeated herein.

As shown in FIG. 4, pre-simulation images of the first model and the second model may be displayed on a user interface (UI) 430 of a console of a medical linear accelerator. If a simulation result indicates that the first component may collide with the second component, processing may be performed in the manner described at step S103. In addition to a display module 431 displaying the pre-simulation images, a module 432 relating to collision processing may also be displayed on the UI 430 to, for example, prompt a user that a collision will occur.

As shown in FIG. 5, real-time simulation images of the first model and the second model may also be displayed on the UI 430 of a console of a medical linear accelerator. If a simulation result indicates that the first component may collide with the second component, processing may be performed in the manner as described in step S103.

Similarly, for a real-time detection process including a subject to be treated, the following may also be included in the example: for each of the detection timings, whether the first component and the subject collide with each other is determined based on the spatial position of the first model, the spatial position of the third model, and the collision condition.

When the movement process of each component is simulated approximately synchronously at step S202, for each detection timing during a movement process, the spatial positions of the first model at a detection period subsequent to a particular detection timing and the spatial position of the third model at the particular detection timing are determined. Then, whether the first model and the third model contact with each other at the detection period in the simulation environment is determined based on the spatial positions of the first model at the detection period and the spatial position of the third model at the particular detection timing. If it is determined that the first model and the third model contact with each other at the detection period in the simulation environment, it is determined that the first component will collide with the subject in the detection period, otherwise it is determined that no collision will occur.

Further, if a real-time detection result indicates that the first component will collide with the subject in the detection period, a corresponding operation plan of the target system is terminated. That is, each moving component is stopped. And also prompt information representing "human body collision may occur" may be output by voice, lamp light, text, or a combination thereof to prompt a user to perform further processing.

To sum up, in a method of detecting collision provided by the example of the present disclosure, a movable component to be detected is taken as the first component, a movable component or an immovable component other than the first component is taken as a second component. A first model is obtained by performing modelling based on an exterior shape of the first component, and a second model is obtained by performing modelling based on an exterior shape of the second component. Then, a radiotherapy treatment plan of a subject to be treated is obtained. For each of detection timings, a spatial position of the first model and a spatial position of the second model may be determined based on the movement process of the first component recorded in the radiotherapy treatment plan. For each of the detection timings, whether the first component and the second component collide with each other is determined based on the spatial position of the first model, the spatial position of the second model, and a collision condition. Further, in a real (or practical) operating process, modelling may also be performed for a subject to detect whether a collision may occur between the component and the subject. It can be seen that whether a collision will occur between the components and between the component and the subject may be determined by simulating the spatial positions of the components and the subject without using a collision-sensing apparatus.

THIRD EXAMPLE

The specific implementations of step S103 of the first example or step S203 of the second example will be described in further detail herein.

Figure 6:
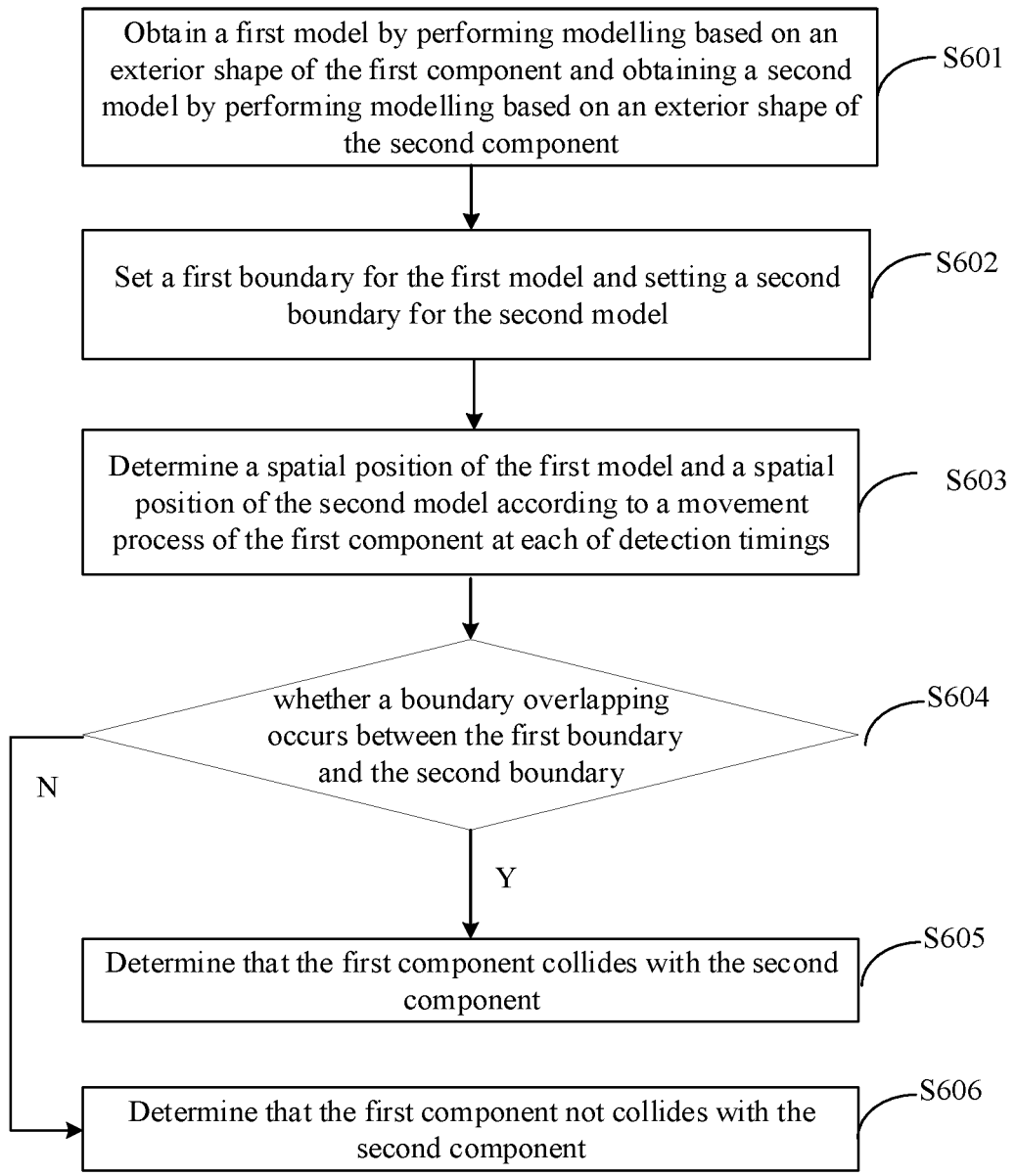
FIG. 6 is a flowchart illustrating a process of a method of detecting collision according to still another example of the present disclosure.

FIG. 6 illustrates a flowchart of a process of a method of detecting collision according to the example. The method of detecting collision may include the following steps.

At step S601, a first model is obtained by performing modelling based on an exterior shape of a first component and a second model is obtained by performing modelling based on an exterior shape of a second component.

It is noted that step S601 is consistent with step S101 in the first example or step S201 in the second example and a reference may be made to descriptions of the first example or the second example for related parts which are not repeated herein.

At step S602, a first boundary is set for the first model and a second boundary is set for the second model. A first boundary gap exists between the first boundary and a boundary of the first model, and a value of the first boundary gap is equal to or greater than zero. A second boundary gap exists between the second boundary and a boundary of the second model, and a value of the second boundary gap is equal to or greater than zero.

Figure 7A:
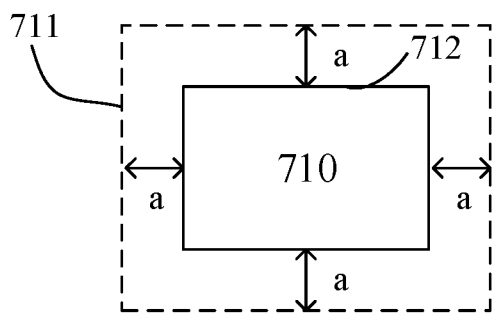
FIG. 7A is a schematic diagram illustrating a first boundary gap according to an example of the present disclosure.

As shown in FIG. 4 and FIG. 5, after the first model is built in a 3D simulation environment, a first boundary may be set for the first model. A first boundary gap exists between the first boundary and a boundary of the first model and a value of the first boundary gap is equal to or greater than zero. In a case that the value of the first boundary gap is equal to zero, a range enclosed by the first boundary is consistent with exterior shape of the first model. In a case that the value of the first boundary gap is greater than zero, a range enclosed by the first boundary includes the first model. For example, the value of the first boundary gap 412 is set in a parameter-setting module 410. Then the first boundary may be set by setting the value of the first boundary gap 412 in a collider assembly of the first model 421. As shown in FIG. 7A, in the case that the value of the first boundary gap a is set to zero, it indicates that the boundary 712 of the first model 710 is completely same as the first boundary 711; in the case that the value of the first boundary gap a is set to be greater than zero, it indicates that the boundary 712 of the first model 710 is within the first boundary 711.

Figure 7B:
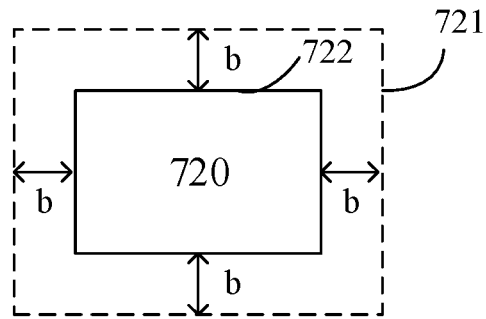
FIG. 7B is a schematic diagram illustrating a second boundary gap according to an example of the present disclosure.

Similarly, as shown in FIG. 4 and FIG. 5, after the second model is built in a 3D simulation environment, a second boundary may be set for the second model. A second boundary gap exists between the second boundary and a boundary of the second model and a value of the second boundary gap is equal to or greater than zero. In a case that the value of the second boundary gap is equal to zero, a range enclosed by the second boundary is consistent with exterior shape of the second model. In a case that the value of the second boundary gap is greater than zero, a range enclosed by the second boundary includes the second model. For example, the value of the second boundary gap 412 is set in a parameter-setting module 410. Then the second boundary may be set by setting the value of the second boundary gap 412 in a collider assembly of the second model 421. As shown in FIG. 7B, in the case that the value of the second boundary gap b is set to zero, it indicates that the boundary 722 of the second model 720 is completely same to the second boundary 721; in the case that the value of the second boundary gap b is set to be greater than zero, it indicates that the boundary 722 of the second model 720 is within the second boundary 721.

To detect whether the first component collides with the second component, the value of the first boundary gap a and the value of the second boundary gap b may both be set to zero so that the boundary of the first model is overlapped with the first boundary and the boundary of the second model is overlapped with the second boundary.

Further, a first distance threshold L may be assigned for collision detection of respective components to better solve the problem of different component tolerances in actual use, where the first distance threshold L is a value larger than zero. The value of the first boundary gap a and the value of the second boundary gap b can be determined based on the first distance threshold L. Specifically, if the first distance threshold is L, the value of the first boundary gap a may be equal to the first distance threshold L, or the value of the second boundary gap b may be equal to the first distance threshold L, or a sum of the value of the first boundary gap a and the value of the second boundary gap b is equal to the first distance threshold L.

It is noted that the value of the first boundary gap a, the value of the second boundary gap b, and the first distance threshold L may be pre-configured in a configuration file. When the example is implemented, the parameters may be read from the configuration file. Of course, the parameters may also be set by a user.

At step S603, a spatial position of the first model and a spatial position of the second model are determined based on a movement process of the first component at each detection timing.

It is noted that step S603 is consistent with step S102 in the first example and a reference may be made to the descriptions of the first example for related parts which are not repeated herein. Of course, step S603 may also be implemented by adopting step S202 in the second example and a reference may be made to the descriptions of the second example for related parts which are not repeated herein.

At step S604, for each of the detection timings, whether a boundary overlapping occurs between the first boundary and the second boundary is determined according to the spatial position of the first model and the spatial position of the second model. For example, a spatial position of the first boundary can be determined based on the spatial position of the first model and the first boundary gap a, and a spatial position of the second boundary can be determined based on the spatial position of the second model and the second boundary gap b. Whether the boundary overlapping occurs between the first boundary and the second boundary can be determined based on the spatial position of the first boundary and the spatial position of the second boundary.

Figure 8A:
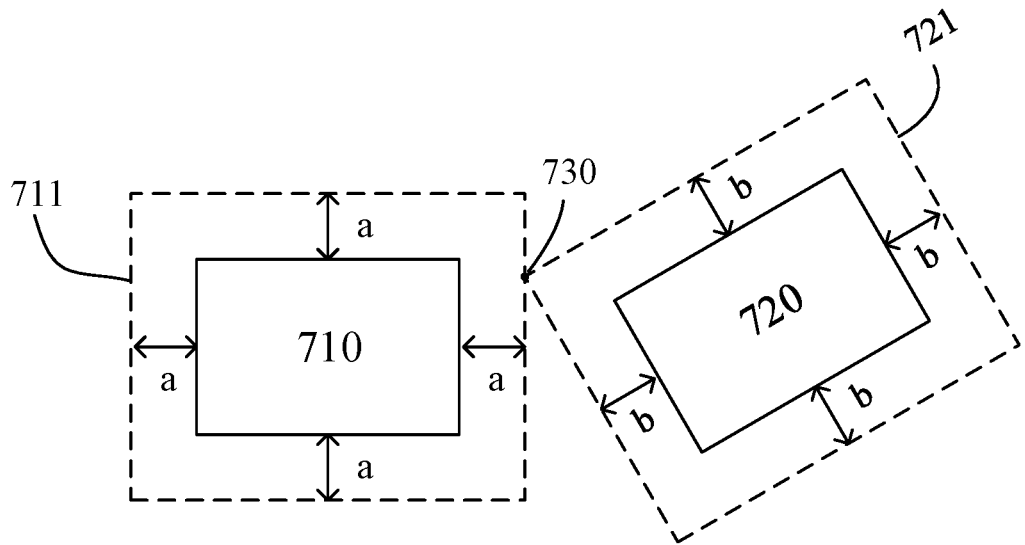
FIG. 8A is a schematic diagram illustrating a point contact according to an example of the present disclosure.
Figure 8B:
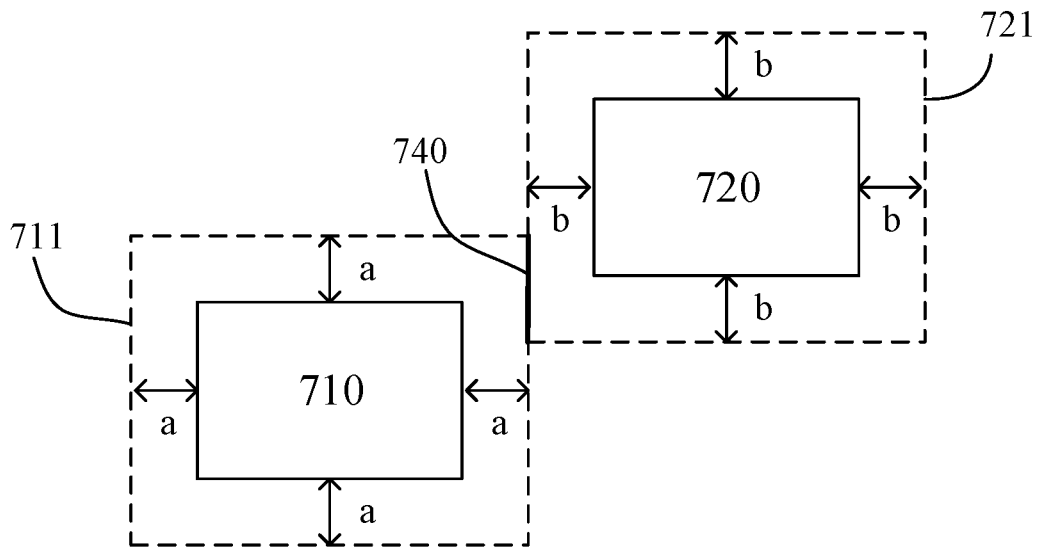
FIG. 8B is a schematic diagram illustrating a line contact or a surface contact according an example of the present disclosure.
Figure 8C:
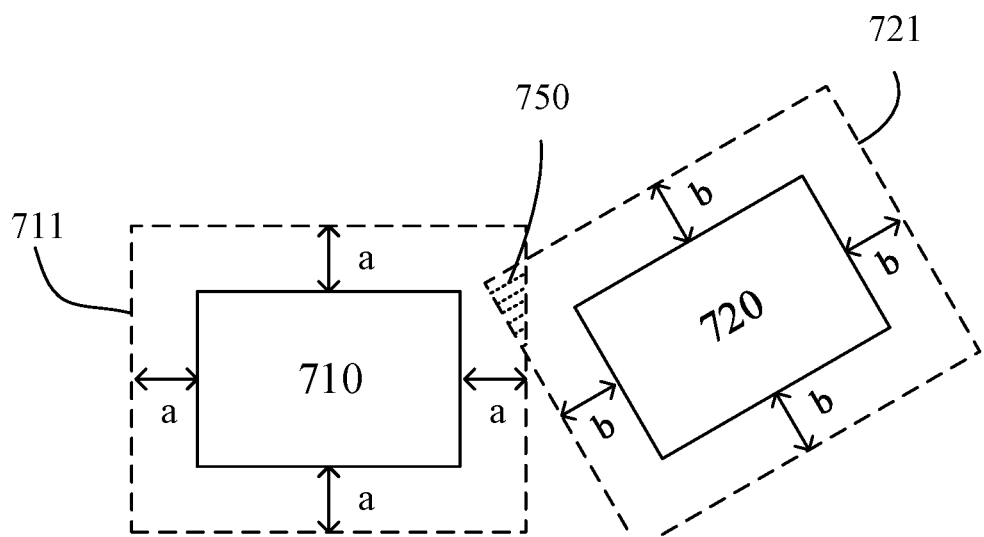
FIG. 8C is a schematic diagram illustrating a block contact according to an example of the present disclosure.

In the step, a boundary overlapping between the first boundary and the second boundary refers to that the first boundary contacts with the second boundary, that is, point contact, line contact, surface contact, or block contact occurs between the first boundary and the second boundary. As shown in FIG. 8A, when one or more contact points 730 exist between the first boundary 711 and the second boundary 721, it is determined that a point contact occurs. As shown in FIG. 8B, when a contact part between the first boundary 711 and the second boundary 721 forms a line 740, it is determined that a line contact occurs. Also as shown in FIG. 8B, when a contact part between the first boundary 711 and the second boundary 721 forms a surface 740 (the surface is not shown because the FIG. 8B is a 2D diagram), it is determined that a surface contact occurs. In addition, if the value of the first boundary gap a and/or the value of the second boundary gap b are set to be greater than zero, when a contact part between the first boundary 711 and the second boundary 721 forms a block 750 as shown in FIG. 8C, it is determined that a block contact occurs.

At step S605, if the boundary overlapping occurs between the first boundary and the second boundary, it is determined that the first component collides with the second component.

At step S606, if no boundary overlapping occurs between the first boundary and the second boundary, it is determined that the first component does not collide with the second component.

When a point contact, a line contact, a surface contact, or a block contact occurs between the first boundary and the second boundary in a 3D simulation environment, it indicates that the first model and the second model contact with each other, which further indicates that the first component collides with the second component, otherwise indicates that the first component does not collide with the second component.

Further, this example may also include the subject in the second example, that is, the third model for the subject. A third boundary may also be set for the third model at step S602 in the example.

Figure 9:
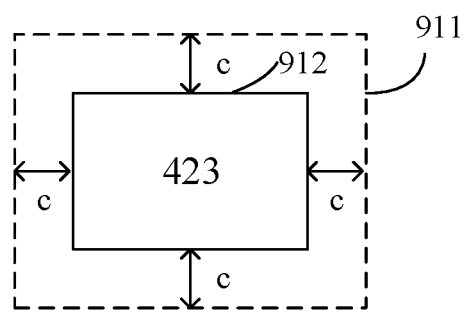
FIG. 9 is a schematic diagram illustrating a third boundary gap according to an example of the present disclosure.

As shown in FIG. 5, after the third model is built in a 3D simulation environment, a third boundary may be set for the third model. A third boundary gap exists between the third boundary and a boundary of the third model, and a value of the third boundary gap is equal to or greater than zero. In a case that the value of the third boundary gap is equal to zero, a range enclosed by the third boundary is consistent with exterior shape of the third model. In a case that the value of the third boundary gap is greater than zero, a range enclosed by the third boundary includes the third model. For example, the value of the third boundary gap 412 is set in a parameter-setting module 410. Then the third boundary may be set by setting the value of the third boundary gap 412 in a collider assembly of the third model 423. As shown in FIG. 9, in the case that the value of third boundary gap c is set to zero, it indicates that the boundary 912 of the third model 423 is completely same to the third boundary 911; in the case that the value of the third boundary gap c is set to be greater than zero, it indicates that the boundary 912 of the third model 423 is within the third boundary 911.

To detect whether the first component collides with the subject, the value of the first boundary gap a and the value of the third boundary gap c may both be set to zero so that the boundary of the first model is overlapped with the first boundary and the boundary of the third model is overlapped with the third boundary.

Further, a second distance threshold M may be assigned for collision detection between the first component and the subject to better solve the problem of different component tolerances in actual use, where the second distance threshold M is a value larger than zero. The second distance threshold M may be the same as the first distance threshold L, or different from the first distance threshold L. The value of the first boundary gap a and the value of the third boundary gap c can be determined based on the second distance threshold M Specifically, the value of the first boundary gap a may be equal to the second distance threshold M, or the value of the third boundary gap c may be equal to the second distance threshold M, or a sum of the value of the first boundary gap a and the value of the third boundary gap c is equal to the second distance threshold M.

It is noted that the value of the third boundary gap c, and the second distance threshold M may be pre-configured in a configuration file. When the example is implemented, the parameters may be read from the configuration file. Of course, the parameters may also be set by a user.

Based on this, determining whether the first component collides with the subject may include the followings.

A spatial position of the first model and a spatial position of the third model are determined based on a movement process of the first component at each detection timing.

For each of the detection timings, whether a boundary overlapping occurs between the first boundary and the third boundary is determined according to the spatial position of the first model and the spatial position of the third model. For example, a spatial position of the first boundary can be determined based on the spatial position of the first model and the first boundary gap a, and a spatial position of the third boundary can be determined based on the spatial position of the third model and the third boundary gap c. Whether the boundary overlapping occurs between the first boundary and the third boundary can be determined based on the spatial position of the first boundary and the spatial position of the third boundary.

If the boundary overlapping occurs between the first boundary and the third boundary, it is determined that the first component collides with the subject.

If no boundary overlapping occurs between the first boundary and the third boundary, it is determined that the first component does not collide with the subject.

It is noted that the steps are similar to the above steps S603-S606 and therefore, the second boundary at steps S603-606 can be replaced with the third boundary. In addition, for the determination of the spatial position of the third model, a reference may be made to the descriptions of the second example for related parts which are not repeated herein.

When a point contact, a line contact, a surface contact, or a block contact occurs between the first boundary and the third boundary in a 3D simulation environment, it indicates that contact occurs between the first model and the third model, which further indicates that the first component will collide with the subject, otherwise indicates that the first component does not collide with the subject.

To sum up, in the method of detecting collision provided in the example, a movable component to be detected is taken as the first component, a movable component or an immovable component other than the first component is taken as a second component. A first model is obtained by performing modelling based on an exterior shape of the first component and a second model is obtained by performing modelling based on an exterior shape of the second component. A first boundary is set for the first model and a second boundary is set for the second model. Then, the spatial position of the first model and the spatial position of the second model may be determined at each detection timing based on a movement process of the first component. For each of the detection timings, whether boundary overlap occurs between the first boundary and the second boundary is determined according to the spatial position of the first model and the spatial position of the second model. In response to determining that boundary overlap occurs between the first boundary and the second boundary, it is determined that the first component collides with the second component. Further, in a practical operation process, modelling may be performed for a subject to be treated. Whether a collision will occur between the first component and the subject is determined by determining whether the first boundary overlaps a third boundary which is set for the subject. It can be seen that whether a collision will occur between components and between component and the subject may be determined by simulating the spatial positions of the components and the subject without using a collision-sensing apparatus.

FOURTH EXAMPLE

Based on the method of detecting collision provided by the above examples, an apparatus for detecting collision is also provided by an example of the present disclosure, which will be detailed below in combination with accompanying drawings.

Figure 10:
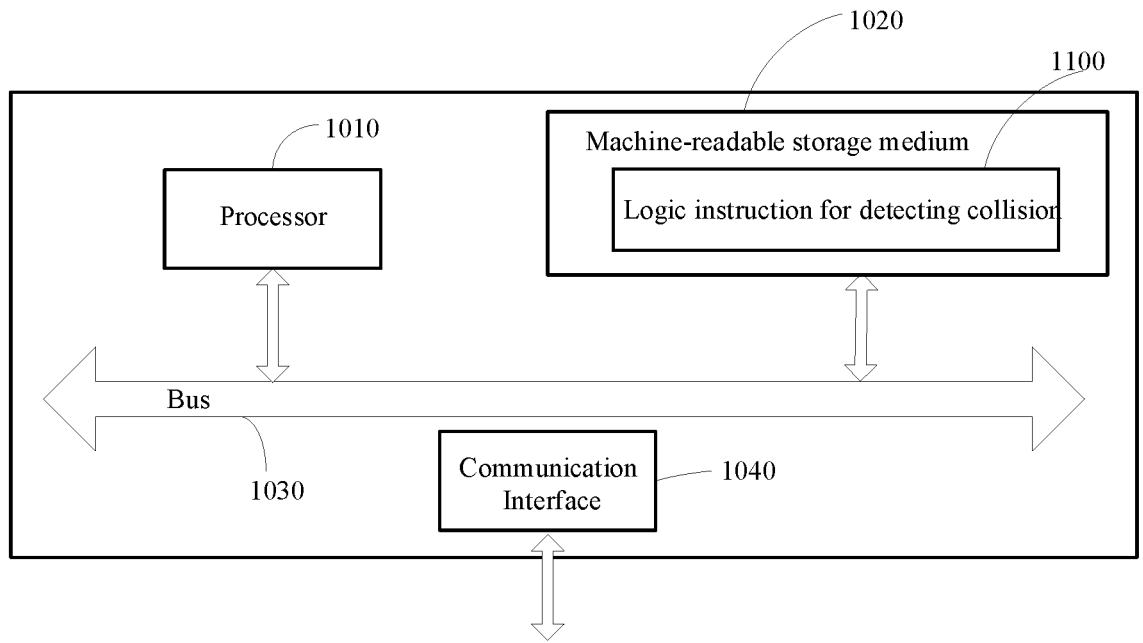
FIG. 10 is a schematic diagram illustrating a hardware structure of an apparatus for detecting collision according to an example of the present disclosure.

FIG. 10 is a schematic diagram illustrating a hardware structure of an apparatus for detecting collision according to the example of the present disclosure. The apparatus for detecting collision may include a processor 1010 and a machine readable storage medium 1020, where the processor 1010 and the machine readable storage medium 1020 can be connected with each other via an internal bus 1030. In other possible implementations, the apparatus may also include an external interface 1040 to communicate with other devices or components. The apparatus being applied to a target system comprising at least one movable component, where a movable component to be detected is taken as a first component, a movable component or an immovable component other than the first component is taken as a second component.

In different examples, the machine readable storage medium 1020 is a non-transitory memory. For example, a flash memory, a storage drive (e.g. hard disk drive), a solid state disk, any type of storage disk (e.g., compact disk, Digital Video Disk (DVD)), or a similar storage medium, or a combination thereof. The machine readable storage medium 1020 may also include different transitory memories such as Random Access Memory (RAM) to cooperate with the non-volatile memory and the processor.

Figure 11:
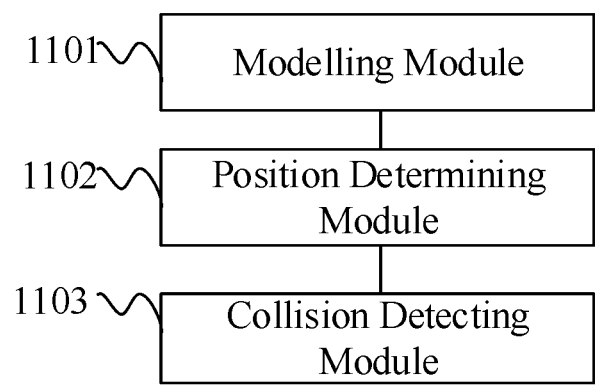
FIG. 11 is a structural diagram illustrating function modules of logic instructions for detecting collision according to an example of the present disclosure.

Further, the machine readable storage medium 1020 stores logic instructions 1100 for collision detection. As shown in FIG. 11, functionally, the logic instructions may include a modelling module 1101, a position determining module 1102 and a collision detecting module 1103.

The modelling module 1101 is configured to obtain a first model by performing modelling based on exterior shape of the first component, and obtain a second model by performing modelling based on exterior shape of the second component.

The position determining module 1102 is configured to determine a spatial position of the first model and a spatial position of the second model according to a movement process of the first component at each of detection timings.

The collision detecting module 1103 is configured to for each of the detection timings, determine whether the first component collides with the second component according to the spatial position of the first model, the spatial position of the second model and a collision condition.

The apparatus provided by the present disclosure may detect whether a collision occurs between components by simulating spatial positions of the components without using a collision sensing apparatus.

A software implementation is taken as an example below to further describe how the apparatus for detecting collision executes the logic instruction 1100. In this example, the logic instructions 1100 should be understood as a machine executable instruction stored in the machine readable storage medium 1020. When a processor 1010 of a medical linear accelerator system in the present disclosure executes the logic instructions 1100, the processor 1010 performs the following operations by invoking the logic instruction 1100 stored in the machine readable storage medium 1020.

A first model is obtained by performing modelling based on exterior shape of the first component.

A second model is obtained by performing modelling based on exterior shape of the second component;

A spatial position of the first model and a spatial position of the second model are determined according to a movement process of the first component at each of detection timings.

For each of the detection timings, whether the first component collides with the second component is determined according to the spatial position of the first model, the spatial position of the second model and a collision condition.

In one implementation, the target system is a medical linear accelerator system, the first component is a treatment head of the medical linear accelerator system, the second component is a treatment bed of the medical linear accelerator system. When determining the spatial position of the first model and the spatial position of the second model, the followings may be specifically included.

A radiotherapy treatment plan of a subject to be treated is obtained.

The spatial position of the first model and the spatial position of the second model are determined according to a movement process of the first component recorded in the radiotherapy treatment plan at each of the detection timings.

Further, during a process of performing treatment for the subject according to the radiotherapy treatment plan, a third model is obtained by performing modelling based on exterior shape of the subject.

Further, the followings may be specifically included.

A spatial position of the third model is determined at each of the detection timings.

For each of the detection timings, whether the first component collides with the subject is determined according to the spatial position of the first model, the spatial position of the third model and the collision condition.

Further, when obtaining the third model by performing modelling based on the exterior shape of the subject, the followings may be specifically included.

Three-dimension image data of the subject is obtained with a 3D camera.

The third model by performing modelling is obtained based on the three-dimension image data.

In one implementation, when determining whether the first component collides with the second component, the followings may be specifically included.

A first boundary is set for the first model, where there is a first boundary gap between the first boundary and a boundary of the first model, and a value of the first boundary gap is equal to or greater than zero.

A second boundary is set for the second model, where there is a second boundary gap between the second boundary and a boundary of the second model, and a value of the second boundary gap is equal to or greater than zero.

For each of the detection timings, whether a boundary overlapping occurs between the first boundary and the second boundary is determined according to the spatial position of the first model and the spatial position of the second model.

In response to the boundary overlapping between the first boundary and the second boundary, the first component collides with the second component is determined.

Further, in a case that the value of the first boundary gap is equal to zero, a range enclosed by the first boundary is consistent with the exterior shape of the first model; in a case that the value of the first boundary gap is greater than zero, a range enclosed by the first boundary comprises the first mode; in a case that the value of the second boundary gap is equal to zero, a range enclosed by the second boundary is consistent with the exterior shape of the second model; and in a case that the value of the second boundary gap is greater than zero, a range enclosed by the second boundary comprises the second model.

Further, the boundary overlapping includes any of: a point contact, a line contact, a surface contact, and a block contact.

In one implementation, when determining whether the first component collides with the subject, the followings may be specifically included.

A first boundary is set for the first model, where, there is a first boundary gap between the first boundary and a boundary of the first model, and a value of the first boundary gap is equal to or greater than zero.

A third boundary is set for the subject, where, there is a third boundary gap between the third boundary and a boundary of the third model, and a value of the third boundary gap is equal to or greater than zero.

For each of the detection timings, whether a boundary overlapping occurs between the first boundary and the third boundary is determined according to the spatial position of the first model and the spatial position of the third model.

In response to the boundary overlapping between the first boundary and the third boundary, the first component collides with the subject is determined. Further, in a case that the value of the first boundary gap is equal to zero, a range enclosed by the first boundary is consistent with the exterior shape of the first model; in a case that the value of the first boundary gap is greater than zero, a range enclosed by the first boundary comprises the first mode; in a case that value of the third boundary gap is equal to zero, a range enclosed by the third boundary is consistent with the exterior shape of the third model; and in a case that value of the third boundary gap is greater than zero, a range enclosed by the third boundary comprises the third model.

Further, the boundary overlapping includes any of: a point contact, a line contact, a surface contact, and a block contact.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. A method of detecting collision for a target system comprising at least one movable component, the method comprising:
   obtaining a first model by performing modelling based on an exterior shape of a first component in the target system, the first component being a movable component;
   obtaining a second model by performing modelling based on an exterior shape of a second component in the target system, the second component being different from the first component;
   determining a spatial position of the first model and a spatial position of the second model according to a movement process of the first component at each of detection timings; and
   for each of the detection timings, determining whether the first component collides with the second component in the real movement process at the detection timing according to the spatial position of the first model, the spatial position of the second model, and a collision condition,
   wherein the detection timings are predefined to be a plurality of discrete timings in a time period of the movement process, adjacent discrete timings of the plurality of discrete timings being separated with a predefined time interval.

2. The method of claim 1, wherein determining whether the first component collides with the second component comprises: determining whether the spatial position of the first model and the spatial position of the second model satisfy the collision condition, and
   wherein the collision condition refers to that the first model and the second model contact with each other.

3. The method of claim 1, wherein the movement process of the first component is pre-simulated before a real movement process of the first component.

4. The method of claim 1, wherein the movement process of the first component is simulated approximately synchronously with a real movement process of the first component.

5. The method of claim 4, further comprising:
   for each of the detection timings in the movement process, determining the spatial position of the first model and the spatial position of the second model at a detection period subsequent to the detection timing;
   determining whether the first model and the second model contact with each other at the detection period in a simulation based on the spatial position of the first model and the spatial position of the second model at the detection period; and
   determining whether the first component will collide with the second component at the detection period in the real movement process based on a result of determining whether the first model and the second model contact with each other at the detection period in the simulation.

6. The method of claim 5, further comprising:
   in response to determining that the first component will collide with the second component at the detection period in the real movement process, terminating a corresponding operation plan of the target system by at least one of stopping each moving component in the target system or prompting safety warning information to a user.

7. The method of claim 1, further comprising:
   setting a first rigidbody assembly and a first collider assembly for the first model; and setting a second rigidbody assembly and a second collider assembly for the second model, wherein a collision is triggered by the first and second models respectively added with the first and second rigidbody assemblies and the first and second collider assemblies.

8. The method of claim 1, wherein determining whether the first component collides with the second component comprises:

setting a first boundary for the first model, wherein, there is a first boundary gap between the first boundary and a boundary of the first model, and a value of the first boundary gap is equal to or greater than zero;

setting a second boundary for the second model, wherein, there is a second boundary gap between the second boundary and a boundary of the second model, and a value of the second boundary gap is equal to or greater than zero;

for each of the detection timings, determining whether a boundary overlapping occurs between the first boundary and the second boundary according to the spatial position of the first model and the spatial position of the second model; and in response to determining that the boundary overlapping occurs between the first boundary and the second boundary, determining that the first component collides with the second component.

9. The method of claim 8, wherein, when the value of the first boundary gap is equal to zero, a range enclosed by the first boundary is consistent with the exterior shape of the first model;

when the value of the first boundary gap is greater than zero, a range enclosed by the first boundary comprises the first model;

when the value of the second boundary gap is equal to zero, a range enclosed by the second boundary is consistent with the exterior shape of the second model; and when the value of the second boundary gap is greater than zero, a range enclosed by the second boundary comprises the second model.

10. The method of claim 8, wherein determining whether a boundary overlapping occurs between the first boundary and the second boundary comprises:

determining a spatial position of the first boundary based on the spatial position of the first model and the value of the first boundary gap;

determining a spatial position of the second boundary based on the spatial position of the second model and the value of the second boundary gap; and determining whether the boundary overlapping occurs between the first boundary and the second boundary based on the spatial position of the first boundary and the spatial position of the second boundary.

11. The method of claim 8, wherein the boundary overlapping comprises any one of:

a point contact, a line contact, a surface contact, and a block contact.

12. The method of claim 1, wherein the target system comprises a medical linear accelerator system, the first component comprises a treatment head of the medical linear accelerator system, and the second component comprises a treatment bed of the medical linear accelerator system, and wherein determining the spatial position of the first model and the spatial position of the second model comprises:

obtaining a radiotherapy treatment plan of a subject to be treated; and determining the spatial position of the first model and the spatial position of the second model according to the movement process of the first component recorded in the radiotherapy treatment plan at each of the detection timings.

13. The method of claim 12, further comprising:

during a process of performing treatment for the subject according to the radiotherapy treatment plan, obtaining a third model by performing modelling based on an exterior shape of the subject.

14. The method of claim 13, further comprising:

determining a spatial position of the third model at each of the detection timings; and for each of the detection timings, determining whether the first component collides with the subject according to the spatial position of the first model, the spatial position of the third model and the collision condition.

15. The method of claim 13, wherein obtaining the third model by performing modelling based on the exterior shape of the subject comprises:

obtaining three-dimension (3D) image data of the subject with a 3D camera; and obtaining the third model by performing the modelling based on the three-dimension image data of the subject.

16. The method of claim 15, further comprising:

at each of the detection timings, determining a spatial position of the third model based on the movement process of the first component; and adjusting the spatial position of the third model based on dynamic 3D image data of the subject real-time transmitted from the 3D camera.

17. The method of claim 13, wherein determining whether the first component collides with the subject comprises:

setting a first boundary for the first model, wherein, there is a first boundary gap between the first boundary and a boundary of the first model, and a value of the first boundary gap is equal to or greater than zero;

setting a third boundary for the subject, wherein, there is a third boundary gap between the third boundary and a boundary of the third model, and a value of the third boundary gap is equal to or greater than zero;

for each of the detection timings, determining whether a boundary overlapping occurs between the first boundary and the third boundary according to the spatial position of the first model and the spatial position of the third model; and in response to determining that the boundary overlapping occurs between the first boundary and the third boundary, determining that the first component collides with the subject.

18. The method of claim 17, wherein the boundary overlapping comprises any one of:

a point contact, a line contact, a surface contact, and a block contact.

19. The method of claim 13, wherein the movement process of the first component is simulated approximately synchronously with a real movement process of the first component, and wherein the method further comprises:

for each of the detection timings in the movement process, determining the spatial position of the first model at a detection period subsequent to the detection timing and the spatial position of the third model at the detection timing;

determining whether the first model and the third model contact with each other at the detection period in a simulation based on the spatial position of the first model at the detection period and the spatial position of the third model at the detection timing; and determining whether the first component will collide with the third component at the detection period in the real movement process based on a result of determining whether the first model and the third model contact with each other at the detection period in the simulation.

20. The method of claim 1, wherein, for each of the detection timings, a duration of the detection period comprises at least an interval between the detection timing and a detection timing next to the detection timing.

21. An apparatus for detecting collision for a target system comprising at least one movable component, the apparatus comprising:

at least one processor; and at least one non-transitory machine readable storage medium coupled to the at least one processor having machine-executable instructions stored thereon that, when executed by the at least one processor, cause the at least one processor to perform operations comprising:

obtaining a first model by performing modelling based on an exterior shape of a first component in the target system, the first component being a movable component;

obtaining a second model by performing modelling based on an exterior shape of a second component in the target system, the second component being different from the first component;

determining a spatial position of the first model and a spatial position of the second model according to a movement process of the first component at each of detection timings; and for each of the detection timings, determining whether the first component collides with the second component according to the spatial position of the first model in the real movement process at the detection timing, the spatial position of the second model, and a collision condition, wherein the detection timings are predefined to be a plurality of discrete timings in a time period of the movement process, adjacent discrete timings of the plurality of discrete timings being separated with a predefined time interval.

* * * * *